United States Patent
Man et al.

(10) Patent No.: US 8,034,759 B2
(45) Date of Patent: Oct. 11, 2011

(54) ENHANCED STABILITY PERACID COMPOSITIONS

(75) Inventors: Victor F. Man, St. Paul, MN (US); Keith G. LaScotte, Maplewood, MN (US); Yvonne M. Killeen, South St. Paul, MN (US); Steven E. Lentsch, St. Paul, MN (US)

(73) Assignee: Ecolab USA Inc., St. Paul, MN (US)

( * ) Notice: Subject to any disclaimer, the term of this patent is extended or adjusted under 35 U.S.C. 154(b) by 79 days.

(21) Appl. No.: 12/262,935

(22) Filed: Oct. 31, 2008

(65) Prior Publication Data

US 2010/0108942 A1    May 6, 2010

(51) Int. Cl.
| | |
|---|---|
| C11D 3/02 | (2006.01) |
| C11D 7/18 | (2006.01) |
| C11D 7/54 | (2006.01) |
| C11D 9/42 | (2006.01) |
| C11D 17/08 | (2006.01) |
| C11D 3/33 | (2006.01) |
| C11D 3/39 | (2006.01) |
| A62D 3/00 | (2007.01) |
| A62D 9/00 | (2006.01) |
| C01B 7/00 | (2006.01) |
| C01B 11/00 | (2006.01) |
| C01B 13/00 | (2006.01) |
| C01B 15/00 | (2006.01) |
| C02F 1/00 | (2006.01) |
| C09K 3/00 | (2006.01) |

(52) U.S. Cl. ........ 510/375; 510/108; 510/367; 510/405; 510/480; 252/186.1; 252/186.25; 252/186.26; 252/186.42

(58) Field of Classification Search ............ 252/186.25–186.26, 186.1, 186.42; 510/477–480, 108, 367, 375, 405

See application file for complete search history.

(56) References Cited

U.S. PATENT DOCUMENTS

| | | | | |
|---|---|---|---|---|
| 3,053,633 | A | * | 9/1962 | Dunlop et al. ................ 423/272 |
| 4,259,200 | A | * | 3/1981 | Sims et al. .................... 510/376 |
| 4,443,352 | A | * | 4/1984 | Broze et al. ...................... 8/137 |
| 4,450,089 | A | * | 5/1984 | Broze et al. .................... 510/313 |
| 4,547,305 | A | * | 10/1985 | Cornelissen et al. ......... 510/376 |
| 5,089,167 | A | | 2/1992 | Coyne et al. |
| 5,091,106 | A | | 2/1992 | Jacobs et al. |
| 5,211,874 | A | | 5/1993 | Haendler et al. |
| 5,258,132 | A | | 11/1993 | Kamel et al. |
| 5,597,791 | A | | 1/1997 | Richards et al. |
| 5,624,634 | A | | 4/1997 | Brougham et al. |
| 5,739,096 | A | * | 4/1998 | Rees ............................ 510/376 |
| 5,846,922 | A | * | 12/1998 | Lagnemo et al. ............. 510/375 |
| 5,900,256 | A | | 5/1999 | Scoville, Jr. et al. |
| 6,008,405 | A | * | 12/1999 | Gray et al. ........................ 562/3 |
| 6,221,209 | B1 | * | 4/2001 | Desprez et al. ................. 162/65 |
| 6,264,790 | B1 | * | 7/2001 | Jakara et al. .................... 162/65 |
| 2001/0000251 | A1 | | 4/2001 | Wei et al. |
| 2003/0150574 | A1 | * | 8/2003 | Paren et al. .................... 162/158 |
| 2004/0002434 | A1 | | 1/2004 | Perkins et al. |
| 2005/0209120 | A1 | * | 9/2005 | Reinhardt et al. ............ 510/312 |
| 2007/0032396 | A1 | * | 2/2007 | Schmiedel et al. ........... 510/302 |

FOREIGN PATENT DOCUMENTS

GB    1456592    11/1976

* cited by examiner

*Primary Examiner* — Lorna M Douyon
*Assistant Examiner* — Tanisha Diggs
(74) *Attorney, Agent, or Firm* — Andrew D. Sorensen; Laura C. Dilorenzo; Amy J. Hoffman

(57) ABSTRACT

The present invention is directed to stabilized peracid compositions. Stabilizing compositions including a metal salt and a chelating agent are added to compositions including peracids. The results stabilized peracid compositions have increased shelf life and storage stability.

13 Claims, 6 Drawing Sheets

ENHANCED STABILITY PERACID COMPOSITIONS

CROSS REFERENCE TO RELATED APPLICATIONS

This application is related to: U.S. patent application Ser. No. 12/114,355, now published as U.S. Patent Application Publication Number 2008/0274932, entitled, "*Composition For In Situ Manufacture Of Insoluble Hydroxide When Cleaning Hard Surfaces And For Use In Automatic Warewashing Machines, And Methods For Manufacturing And Using*"; U.S. patent application Ser. No. 12/114,448, now published as U.S. Patent Application Publication Number 2008/0274939, entitled "*Water Treatment System and Downstream Cleaning Methods*"; U.S. patent application Ser. No. 12/114,327, now published as U.S. Patent Application Publication Number 2008/0274928, entitled "*Water Soluble Magnesium Compounds as Cleaning Agents and Methods of Using Them*"; U.S. patent application Ser. No. 12/114,513, now published as U.S. Patent Application Publication Number 2008/0276967, entitled "*Cleaning Compositions Containing Water Soluble Magnesium Compounds and Methods of Using Them*"; U.S. patent application Ser. No. 12/114,428, now published as U.S. Patent Application Publication Number 2008/0274933, entitled "*MG++ Chemistry and Method for Fouling Inhibition in Heat Processing of Liquid Foods and Industrial Processes*"; U.S. patent application Ser. No. 12/114,329, now published as U.S. Pat. No. 7,709,434, entitled "*Compositions Including Hardness Ion and Gluconate and Methods Employing Them to Reduce Corrosion and Etch*"; U.S. patent application Ser. No. 12/114,342, now published as U.S. Patent Application Publication Number 2008/0300160, entitled "*Compositions Including Hardness Ion and Silicate and Methods Employing Them to Reduce Corrosion and Etch*"; U.S. patent application Ser. No. 12/114,364, now published as U.S. Patent Application Publication Number 2008/0287335, entitled "*Compositions Including Hardness Ion and Threshold Agent and Methods Employing Them to Reduce Corrosion and Etch*"; and U.S. patent application Ser. No. 12/114,385, now published as U.S. Patent Application Publication Number 2008/0274930, entitled "*Warewashing Compositions for Use in Automatic Dishwashing Machines and Method for Using*", all commonly assigned to Ecolab, Inc. The entire contents of these patent applications are hereby expressly incorporated herein by reference including, without limitation, the specification, claims, and abstract, as well as any figures, tables, or drawings thereof.

FIELD OF THE INVENTION

The present invention relates to stabilized peracid compositions, as well as methods of making and using them. Stabilizing compositions can be added to peracid compositions resulting in stabilized peracid compositions.

BACKGROUND

Peracids are known for use as sanitizers, disinfectants, deodorizers, and bleaching agents, among other uses. However, conventional peracids have inherent disadvantages of limited storage stability. The shelf life of peracid products is commonly defined by the peracid storage stability. A desirable shelf life often requires a 90% or higher retention of the initial equilibrium peracid level in the product after 1 year storage at ambient temperature.

Peracid products with an enhanced storage stability/shelf life, would result in fewer products needing to be replaced after extended storage, for example in warehouses, due to peracid degradation. Thus, a need exists for storage stable peracid compositions.

SUMMARY

In some aspects, the present invention provides a stable peracid composition including a peracid; and a stabilizing composition. The stabilizing composition includes a metal salt and a chelating agent, or a pre-formed complex including a metal chelant. The stable peracid composition is substantially stable at room temperature for about 1 year.

In other aspects, the present invention provides a method for forming a substantially stabilized peracid composition. A peracid and a stabilizing composition are mixed together to form the stabilized composition. The stabilizing composition includes a metal salt and a chelating agent, or a pre-formed complex including a metal chelant. The method does not include a drying step.

DETAILED DESCRIPTION

Figure 1:
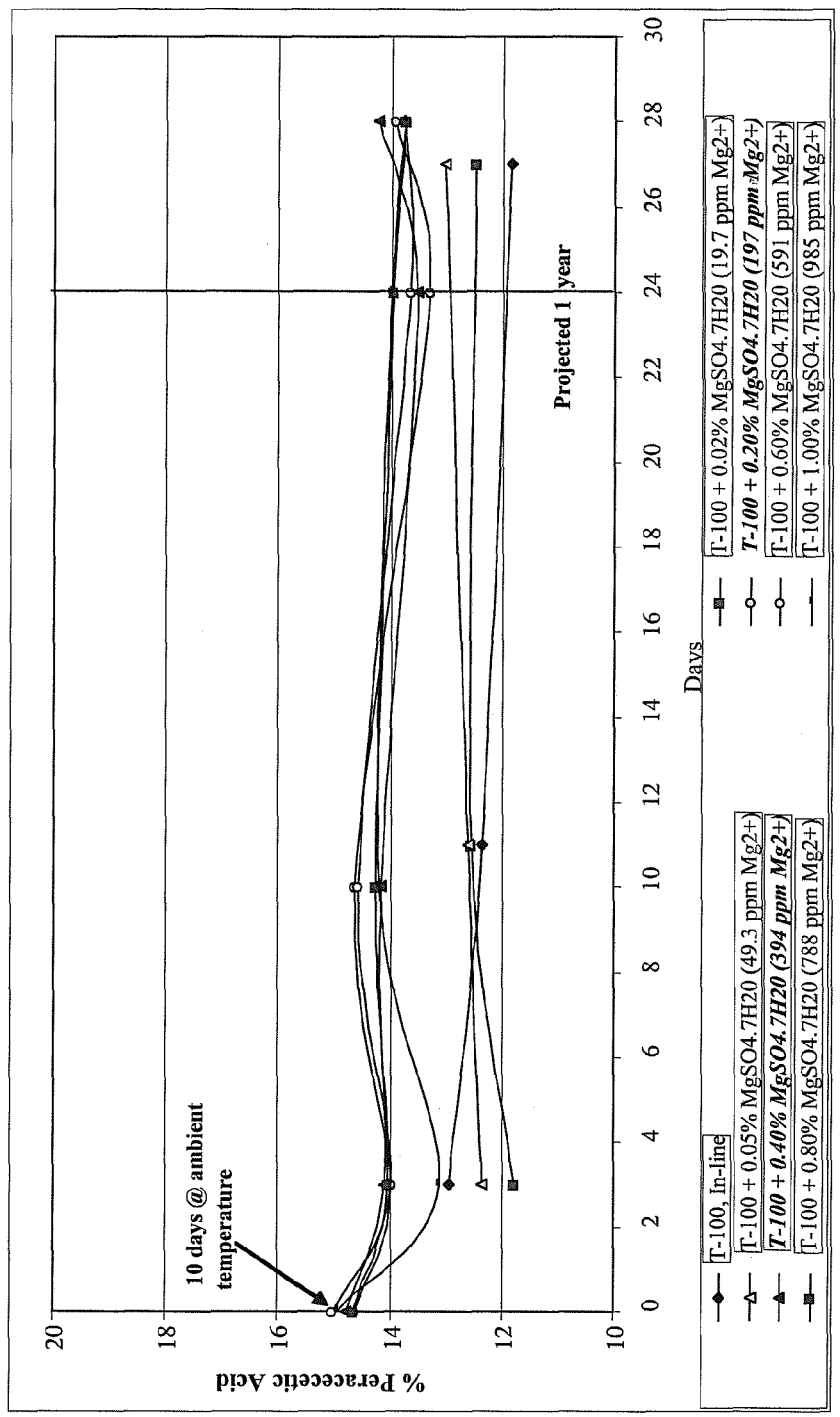
FIG. 1 graphically depicts the results of a storage stability study of a commercially available peracid formulation in combination with a stabilizing composition of the present invention.

In some aspects, the present invention relates to stabilized peracid compositions, as well as methods for making and using stabilized peracid compositions. Peracids are combined with stabilizing compositions resulting in enhanced stability peracid compositions. In some aspects, the stabilizing compositions include an alkaline earth metal and a chelating agent.

So that the invention may be more readily understood certain terms are first defined.

As used herein, the terms "chelating agent" and "sequestrant" refer to a compound that forms a complex (soluble or not) with water hardness ions (from the wash water, soil and substrates being washed) in a specific molar ratio. Chelating agents that can form a water soluble complex include sodium tripolyphosphate, EDTA, DTPA, NTA, citrate, and the like. Sequestrants that can form an insoluble complex include sodium triphosphate, zeolite A, and the like. In some embodiments, 1-Hydroxyethylidene-1,1-Diphosphonic Acid (HEDP) is used as a chelating agent.

As used herein, the term "water soluble" refers to a compound that can be dissolved in water at a concentration of more than 1 wt-%.

As used herein, the terms "slightly soluble" or "slightly water soluble" refer to a compound that can be dissolved in water only to a concentration of 0.1 to 1.0 wt-%.

As used herein, the term "water insoluble" refers to a compound that can be dissolved in water only to a concentration of less than 0.1 wt-%.

As used herein, the term "threshold agent" refers to a compound that inhibits crystallization of water hardness ions from solution, but that need not form a specific complex with the water hardness ion. This distinguishes a threshold agent from a chelating agent or sequestrant. Threshold agents include a polyacrylate, a polymethacrylate, an olefin/maleic copolymer, and the like.

As used herein, the term "free of threshold agent" or "substantially free of threshold agent" refers to a composition, mixture, or ingredient that does not contain a threshold agent or to which only a limited amount of a threshold agent has been added. Should a threshold agent be present, the amount of a threshold agent shall be less than about 7 wt %, less than about 2 wt-%, less then about 0.5 wt-%, or less than about 0.1 wt-%.

As used herein, the term "antiredeposition agent" refers to a compound that helps keep a soil composition suspended in water instead of redepositing onto the object being cleaned.

As used herein, the term "phosphate-free" or "substantially phosphate-free" refers to a composition, mixture, or ingredient that does not contain a phosphate or phosphate-containing compound or to which a phosphate or phosphate-containing compound has not been added. Should a phosphate or phosphate-containing compound be present through contamination of a phosphate-free composition, mixture, or ingredients, the amount of phosphate is less than about 1.0 wt %, less than about 0.5 wt %, less then about 0.1 wt %, or less than about 0.01 wt %.

As used herein, the term "phosphorus-free" or "substantially phosphorus-free" refers to a composition, mixture, or ingredient that does not contain phosphorus or a phosphorus-containing compound or to which phosphorus or a phosphorus-containing compound has not been added. Should phosphorus or a phosphorus-containing compound be present through contamination of a phosphorus-free composition, mixture, or ingredients, the amount of phosphorus is less than about 1.0 wt %, less than about 0.5 wt %, less than about 0.1 wt %, or less than about 0.01 wt %.

By the term "solid" as used to describe a composition of the present invention, it is meant that the hardened composition will not flow perceptibly and will substantially retain its shape under moderate stress or pressure or mere gravity, as for example, the shape of a mold when removed from the mold, the shape of an article as formed upon extrusion from an extruder, and the like. The degree of hardness of the solid composition can range from that of a fused solid block which is relatively dense and hard, for example, like concrete, to a consistency characterized as being malleable and sponge-like, similar to caulking material.

"Cleaning" means to perform or aid in soil removal, bleaching, microbial population reduction, or combination thereof.

As used herein, the term "ware" refers to items such as eating and cooking utensils and other hard surfaces such as showers, sinks, toilets, bathtubs, countertops, windows, mirrors, transportation vehicles, and floors. As used herein, the term "warewashing" refers to washing, cleaning, or rinsing ware.

As used herein, the term "hard surface" includes showers, sinks, toilets, bathtubs, countertops, windows, mirrors, transportation vehicles, floors, and the like. As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of autoclaves and sterilizers, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or fabric surfaces, e.g., knit, woven, and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning using water treated according to the methods of the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning using water treated according to the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, the phrase "food product" includes any food substance that might require treatment with an antimicrobial agent or composition and that is edible with or without further preparation. Food products include meat (e.g. red meat and pork), seafood, poultry, fruits and vegetables, eggs, living eggs, egg products, ready to eat food, wheat, seeds, roots, tubers, leafs, stems, corms, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant" or "plant product" includes any plant substance or plant-derived substance. Plant products include, but are not limited to, seeds, nuts, nut meats, cut flowers, plants or crops grown or stored in a greenhouse, house plants, and the like. Plant products include many animal feeds.

As used herein, the phrase "meat product" refers to all forms of animal flesh, including the carcass, muscle, fat, organs, skin, bones and body fluids and like components that form the animal. Animal flesh includes, but is not limited to, the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and handwash dip-pans, third-sink rinse waters, and the like. Waters also include domestic and recreational waters such as pools, spas, recreational flumes and water slides, fountains, and the like.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "disinfectant" refers to an agent that kills all vegetative cells including most recognized pathogenic microorganisms, using the procedure described in *A. O. A. C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, "weight percent (wt %)", "percent by weight", "% by weight", and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Compositions and Methods of Making

In some aspects, the present invention provides stabilized peracid compositions. As used herein the term "stabilized peracid composition" or "stable peracid composition" or "substantially stable peracid composition" refers to a composition including a peracid or mixture thereof, and a stabilizing composition. The stabilized peracid composition can also include an organic acid and an oxidizing agent, and a stabilizing composition.

In some embodiments, the compositions of the present invention include a peracid forming composition. As used herein the term "peracid forming composition" refers to a composition that produces a peracid when the components of the composition are combined. For example, in some embodiments, a peracid forming composition suitable for use in the present invention includes an organic acid and an oxidizing agent.

The stabilized peracid compositions have an enhanced stability, e.g., increased shelf life, when compared to an equivalent peracid composition that does not include a stabilizing composition. That is, the stabilized peracid compositions retain a higher level of peracid over a given period of time, e.g., a year, than a similar peracid composition that does not include a stabilizing composition.

In some embodiments, the stabilized peracid compositions are substantially stable at room temperature for about one year. In some embodiments, a stabilized peracid composition of the present invention retains at least about 50% of the initial equilibrium peracid level for about 1 year at room temperature. In other embodiments, a stabilized peracid composition of the present invention retains at least about 75% of the initial equilibrium peracid level for about 1 year at room temperature. In still yet other embodiments, the stabilized peracid compositions of the present invention retain about 90% of the initial equilibrium peracid level for about 1 year at room temperature.

In some embodiments, the compositions of the present invention are liquids. In some embodiments, a liquid composition of the invention is substantially non-aqueous (or anhydrous) in character. The term "substantially non-aqueous" as used herein means that while very small amounts of water may be incorporated into such preferred compositions, the amount of water in the non-aqueous liquid detergent compositions of the invention are less than about 30 wt % of the composition. In some embodiments, the water content of the non-aqueous compositions will include less than about 10 wt % by weight.

In other embodiments, the liquid composition according to the present invention is a composition including more than 10 wt % water but less than 90 wt %. The amount of water included in the liquid composition can be for example, less than about 80 wt %, less than about 70 wt %, and less than about 60 wt % by weight of the liquid composition. In some embodiments, the composition can contain water between about 5 wt % and about 50 wt %, about 10 wt % and about 40 wt %, or about 30 wt %. It is to be understood that all values and ranges between these values and ranges are encompassed by the methods of the present invention.

In some aspects, the present invention provides methods for forming a substantially stabilized peracid composition. The method includes mixing or combining a peracid, or a peracid forming composition, and a stabilizing composition. The stabilizing composition includes a metal salt and a chelating agent.

The step of mixing or combining can take place at room temperature, i.e., between about 20° C. and about 25° C. In some embodiments, the stabilized peracid composition is a liquid. In some embodiments, there is no drying step required for forming the stabilized peracid composition.

Stabilizing Compositions

To achieve increased stability and shelf life, a stabilizing composition is added to a composition including a peracid. As used herein the term "stabilizing composition" refers to a composition that increases the shelf life stability of a composition including a peracid. That is, the stabilizing compositions of the present invention, when added to a composition including a peracid or mixture thereof, increase the amount of peracid remaining over a given period of time compared to the same peracid composition that does not include a stabilizing composition.

In some embodiments, the stabilizing compositions of the present invention include a metal salt and a chelating agent. In other embodiments, the stabilizing compositions of the present invention include a pre-formed or pre-reacted complex of a metal chelant. For example, in some embodiments, the stabilizing composition includes a pre-formed complex including a calcium salt of EDTA, or a magnesium salt of EDTA.

Without wishing to be bound by any particular theory, it is thought that the combination of metal salt and chelating agent is needed for stability enhancement. That is, in some instances, a metal salt alone was found to degrade the peracid composition. It was found however, that adding a metal salt to the peracid composition in combination with a chelating agent enhances the stability of the peracid composition more than when a chelating agent alone is used. Thus, a synergy was found when a metal salt and a chelating agent were both used in the stabilizing composition.

In some embodiments, the stabilizing composition has a low mole ratio of metal salt to chelating agent. In some embodiments, the mole ratio of metal salt to chelating agent is about 1:5 to about 1:20, about 1:10 to about 1:15, or about 1:7 to about 1:14. In other embodiments, the ratio of metal salt to chelating agent is about 5:1, about 3:1 or about 1:1. In some embodiments, the ratio of metal salt to chelating agent is about 5:1 to about 1:14. It is to be understood that all values and ranges between these values and ranges are encompassed by the present invention.

Metal Salts

Numerous metal salts are suitable for use in the stabilizing compositions and methods of the present invention. In some embodiments, the metal salt included in the stabilizing composition includes an alkaline earth metal salt. As used herein, the term "alkaline earth metal salt" refers to a compound that is a salt of an alkaline earth metal. Alkaline earth metals are the series of elements including Group II of the periodic table. For example, alkaline earth metals include beryllium (Be), magnesium (Mg), calcium (Ca), strontium (Sr), barium (Ba) and radium (Ra).

In some embodiments, the stabilizing compositions of the present invention include an alkaline earth metal salt including a magnesium salt. Magnesium salts suitable for use in the present invention include both water soluble and water insoluble magnesium salts. In some embodiments, a water soluble magnesium salt is included in the stabilizing composition.

Suitable water soluble magnesium salts for use in the present invention include, but are not limited to, magnesium acetate, magnesium benzoate, magnesium bromide, magnesium bromate, magnesium chromate, magnesium citrate, magnesium formate, magnesium hexafluorosilicate, magnesium iodate, magnesium iodide, magnesium lactate, magnesium molybdate, magnesium nitrate, magnesium perchlorate, magnesium phosphinate, magnesium salicylate, magnesium sulfate, magnesium sulfite, magnesium tartrate, magnesium thiosulfate, a hydrate thereof, and mixtures thereof. These salts can be provided as hydrated salts or anhydrous salts.

Suitable water soluble magnesium compounds include magnesium salts with an anion that also forms a soluble salt with calcium. Such salts include, but are not limited to, magnesium acetate, magnesium benzoate, magnesium bromide, magnesium bromate, magnesium chlorate, magnesium chloride, magnesium chromate, magnesium formate, magnesium iodide, magnesium lactate, magnesium nitrate, magnesium perchlorate, magnesium phosphinate, magnesium salicylate, a hydrate thereof, and a mixture thereof. These salts can be provided as hydrated salts or anhydrous salts.

Water soluble magnesium compounds approved as GRAS for direct food contact include magnesium chloride and magnesium sulfate.

In some embodiments, the stabilizing compositions of the present invention include a water insoluble magnesium salt. Exemplary water insoluble magnesium salts suitable for use in the present invention include, but are not limited to, magnesium borate, magnesium hydrogen phosphate heptahydrate, magnesium oxide, magnesium hydroxide, magnesium fluoride, magnesium carbonate, magnesium carbonate pentahydrate, magnesium phosphate pentahydrate, magnesium carbonate trihydrate, magnesium carbonate hydroxide trihydrate, magnesium oxalate dehydrate, calcium magnesium silicon oxide magnesium mandelate, magnesium borate, magnesium aluminate, magnesium hydroxide, magnesium ferrate, and magnesium silicate. The salts can be provided as hydrated salts or anhydrous salts.

In some embodiments, the stabilizing compositions of the present invention include an alkaline earth metal salt including a calcium salt. Calcium salts suitable for use in the present invention include both water soluble and water insoluble calcium salts.

Calcium salts suitable for use in the present invention, include, but are not limited to, calcium carbonate ($CaCO_3$), calcium hydroxide solution ($Ca(OH)_2$), calcium arsenate ($Ca_3(AsO_4)_2$), calcium carbide ($CaC_2$), calcium cyclamate ($Ca(C_6H_{11}NHSO_3)_2$), calcium gluconate ($Ca(C_6H_{11}O_7)_2$), calcium hypochlorite ($Ca(OCl)_2$), calcium permanganate ($Ca(MnO_4)_2$), calcium phosphate ($Ca_3(PO_4)_2$), calcium phosphide ($Ca_3P_2$), calcium stearate ($Ca(C_{18}H_{35}O_2)_2$), calcium sulfate ($CaSO_4.2H_2O$), calcium tungstate ($CaWO_4$), and Hydroxylapatite ($Ca5(PO4)3(OH)$).

In some embodiments, the metal salt included in the stabilizing composition of the present invention includes a transition metal salt. As used herein the term "transition metal" refers to any element contained within the d-block on the periodic table, i.e., groups 3 through 12 on the periodic table. Exemplary transition metal salts suitable for use in the present invention include, but are not limited to, the salts of zinc, manganese, molybdenum, chromium, copper, iron, cobalt. In some embodiments, the transition metal salt used includes a zinc salt.

In some embodiments, a metal salt is present in the stabilized peracid composition at about 0.01 wt % to about 10 wt %, about 0.05 wt % to about 5 wt, about 0.1 to about 1 wt %, or about 0.2 wt % to about 0.4 wt %. It is to be understood that all values and ranges between these values and ranges are encompassed by the methods of the present invention.

Chelating Agents

In some embodiments, the stabilizing compositions of the present invention include a chelating agent. In some embodiments, the chelating agent includes a phosphonic acid or a phosphonate salt. Suitable phosphonic acids and phosphonate salts include, for example, 1-hydroxy ethylidene-1,1-diphosphonic acid ($CH_3C(PO_3H_2)_2OH$) (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; or mixtures thereof. In some embodiments, the chelating agent includes HEDP.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino (tri(methylenephosphonic acid)), ($N[CH_2PO_3H_2]_3$), available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The chelating agent present in the stabilizing composition can also include an aminocarboxylic acid type sequestrant. Suitable aminocarboxylic acid type sequestrants include, but are not limited to, the acids or alkali metal salts thereof, e.g., amino acetates and salts thereof. Suitable aminocarboxylates include, for example, N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N,N-diacetic acid; and the like; and mixtures thereof Exemplary commercially available chelating agents for use with the present invention include, but are not limited to: sodium tripolyphosphate available from Innophos; Trilon A® available from BASF; Versene 100®, Low NTA Versene®, Versene Powder®, and Versenol 120® all available from Dow; Dissolvine D-40 available from BASF; and sodium citrate.

In some embodiments, a biodegradable aminocarboxylate or derivative thereof is present as a builder in the methods of the present invention. Exemplary biodegradable aminocarboxylates include, but are not limited to: Dissolvine GL-38® and Dissolvine GL-74® both available from Akzo; Trilon M® available from BASF; Baypure CX100® available from Bayer; Versene EDG® available from Dow; HIDS® available from Nippon Shakubai; Octaquest E30® and Octaquest A65® both available from Finetex/Innospec Octel.

In some embodiments, a chelating agent is present in the stabilized peracid composition at about 0.1 wt % to about 10 wt %. In other embodiments, a chelating agent is present in the stabilized peracid composition at about 0.5 wt % to about 5.0 wt %. In still yet other embodiments, a chelating agent is present in the stabilized peracid composition at about 1.0 wt % to about 2.5 wt %. It is to be understood that all values and ranges between these values and ranges are encompassed by the present invention.

Peracid Compositions

In some embodiments the present invention is directed to stabilized peracid compositions. The stabilized peracid compositions of the present invention include at least one peracid, e.g., a peroxycarboxylic acid. In some embodiments, the stabilized compositions of the present invention includes an organic acid and an oxidizing agent.

Peroxycarboxylic Acids

Peroxycarboxylic (or percarboxylic) acids generally have the formula $R(CO_3H)_n$, where, for example, R is an alkyl, arylalkyl, cycloalkyl, aromatic, or heterocyclic group, and n is one, two, or three, and named by prefixing the parent acid with peroxy. The R group can be saturated or unsaturated as well as substituted or unsubstituted. Peroxycarboxylic acids can be made by the direct action of an oxidizing agent on a carboxylic acid, by autoxidation of aldehydes, or from acid chlorides, and hydrides, or carboxylic anhydrides with hydrogen or sodium peroxide.

Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, or the peroxyacids of their branched chain isomers, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof. In some embodiments, the compositions of the invention utilize a combination of several different peroxycarboxylic acids. For example, in some embodiments, the composition includes one or more $C_1$ to $C_4$ peroxycarboxylic acids and one or more $C_5$ to $C_{11}$ peroxycarboxylic acids. Especially preferred is an embodiment in which the $C_1$ to $C_4$ peroxycarboxylic acid is peroxyacetic acid and the $C_5$ to $C_{11}$ acid is peroxyoctanoic acid.

In some embodiments, the compositions and methods of the present invention include peroxyacetic acid. Peroxyacetic (or peracetic) acid is a peroxycarboxylic acid having the formula: $CH_3COOOH$. Generally, peroxyacetic acid is a liquid having an acrid odor at higher concentrations and is freely soluble in water, alcohol, ether, and sulfuric acid. Peroxyacetic acid can be prepared through any number of methods known to those of skill in the art including preparation from acetaldehyde and oxygen in the presence of cobalt acetate. A solution of peroxyacetic acid can be obtained by combining acetic acid with hydrogen peroxide. A 50% solution of peroxyacetic acid can be obtained by combining acetic anhydride, hydrogen peroxide and sulfuric acid.

In some embodiments, the compositions and methods of the present invention include peroxyoctanoic acid, peroxynonanoic acid, or peroxyheptanoic acid, preferably peroxyoctanoic acid. Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid can be prepared through any number of methods known to those of skill in the art. A solution of peroxyoctanoic acid can be obtained by combining octanoic acid and hydrogen peroxide and a hydrotrope, solvent or carrier.

In some embodiments, the compositions of the present invention include about –0.0005 wt % to about 20 wt %, about 0.3 wt % to about 10 wt %, about 0.5 wt % to about 5.0 wt %, about 1wt % to about 3 wt %, or about 1 wt % to about 2 wt % of one or more peroxycarboxylic acids. It is to be understood that all values and ranges between these values and ranges are encompassed by the present invention.

Organic Acids

In some embodiments, the stabilized peracid composition for use with the present invention includes at least one organic acid. Any organic acid capable of forming a peracid can be used in the compositions and methods of the present invention. Suitable organic acids for use with the present invention include, but are not limited to, carboxylic acids.

In some embodiments, the compositions of the present invention include at least one carboxylic acid. In some embodiments, the compositions of the present invention include at least two, at least three, or at least four or more carboxylic acids.

In some embodiments, the carboxylic acid for use with the compositions of the present invention is a $C_1$ to $C_{22}$ carboxylic acid. In some embodiments, the carboxylic acid for use with the compositions of the present invention is a $C_5$ to $C_{11}$ carboxylic acid. In some embodiments, the carboxylic acid for use with the compositions of the present invention is a $C_1$ to $C_4$ carboxylic acid. Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof.

In some embodiments, the compositions of the present invention include about 10 wt % to about 95 wt %, about 25 wt % to about 80 wt %, or about 50 wt % to about 75 wt % of a carboxylic acid. In some embodiments, the compositions of the present invention include about 30 wt % of acetic acid. In other embodiments, the compositions of the present invention include about 5 wt % of octanoic acid. In other embodiments, the compositions of the present invention include a combination of octanoic acid and acetic acid.

Oxidizing Agents

The present composition can include any of a variety of oxidizing agents, for example, hydrogen peroxide. The oxidizing agent can be effective to convert an acid into a peracid. In some embodiments, the oxidizing agent can also have antimicrobial activity. In other embodiments, the oxidizing agent is present in an amount insufficient to exhibit antimicrobial activity.

In some embodiments, the compositions of the present invention include about 0.001 wt % to about 99 wt %, or about 10 wt % to about 60 wt %. In other embodiments, the compositions of the present invention include about 20 wt % or about 50 wt % oxidizing agent. It is to be understood that all ranges and values between these ranges and values are encompassed by the present invention.

Examples of inorganic oxidizing agents include the following types of compounds or sources of these compounds, or alkali metal salts including these types of compounds, or forming an adduct therewith: hydrogen peroxide, or hydrogen peroxide donors of: group 1 (IA) oxidizing agents, for example lithium peroxide, sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2)_2(OH)_4]\cdot 6H_2O$ (also called sodium perborate tetrahydrate); sodium peroxyborate tetrahydrate of the formula $Na_2B_2(O_2)_2[(OH)_4]\cdot 4H_2O$ (also called sodium perborate trihydrate); sodium peroxyborate of the formula $Na_2[B_2(O_2)_2(OH)_4]$ (also called sodium perborate monohydrate); group 14 (IVA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group VIa oxidizing agents such as sodium periodate, potassium perchlorate. Other active inorganic oxygen compounds can include transition metal peroxides; and other such peroxygen compounds, and mixtures thereof.

In some embodiments, the compositions and methods of the present invention employ one or more of the inorganic oxidizing agents listed above. Suitable inorganic oxidizing agents include ozone, hydrogen peroxide, hydrogen peroxide adduct, group IIIA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

Hydrogen peroxide presents one suitable example of an inorganic oxidizing agent. Hydrogen peroxide can be provided as a mixture of hydrogen peroxide and water, e.g., as liquid hydrogen peroxide in an aqueous solution. Hydrogen peroxide is commercially available at concentrations of 35%, 70%, and 90% in water. For safety, the 35% is commonly used. The present compositions can include, for example, about 2 to about 30 wt-% or about 5 to about 20 wt-% hydrogen peroxide.

Water

In some embodiments, the compositions of the present invention can include water. Water can be independently added to the composition or can be provided in the composition as a result of its presence in an aqueous material that is added to the composition. In some embodiments, the composition includes about 1 wt % to about 50 wt % water, about 10 wt % to about 30 wt % water, or about 15 wt % to about 25 wt % water. It is to be understood that all values and ranges between these values and ranges are encompassed by the present invention.

Additional Functional Ingredients

In some embodiments, the compositions of the present invention include at least one additional functional ingredient. Specifically, the compositions of the invention can include surfactants, wetting agents, defoaming agents, thickeners, foaming agents, solidification agents, aesthetic enhancing agents (i.e., colorants (e.g., pigments), odorants, or perfumes), among any number of constituents which can be added to the composition. Such additional functional ingredients can be preformulated with the composition of the invention or added to the stabilized composition after formation.

Wetting or Defoaming Agents

Also useful in the compositions of the invention are wetting and defoaming agents. Wetting agents function to increase the surface contact or penetration activity of the composition of the invention.

Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfonated or sulfated derivatives; fatty acids and/or their soaps such as alkali, alkaline earth metal soaps; and phosphates and phosphate esters such as alkyl and alkaline diphosphates, and tributyl phosphates among others; and mixtures thereof.

In some embodiments, the compositions of the present invention can include antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Kirusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 20 wt-%, from about 0.01 wt-% to 5 wt-%, or from about 0.01 wt-% to about 1 wt-%.

Thickening or Gelling Agents

The compositions of the present invention can include any of a variety of known thickeners. Suitable thickeners include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition. However, as a general guideline, the amount of thickener within the present composition ranges from about 0.1 wt-% to about 5 wt-%, from about 0.1 wt-% to about 1.0 wt-%, or from about 0.1 wt-% to about 0.5 wt-%.

Solidification Agent

The present compositions can include a solidification agent, which can participate in maintaining the compositions in a solid form. Suitable solidification agents include a solid polyethylene glycol (PEG), a solid EO/PO block copolymer, and the like; an amide, such as stearic monoethanolamide, lauric diethanolamide, an alkylamide, or the like; starches that have been made water-soluble through an acid or alkaline treatment process; celluloses that have been made water-soluble; an inorganic agent, or the like; poly(maleic anhydride/methyl vinyl ether); polymethacrylic acid; other generally functional or inert materials with high melting points; and the like.

In certain embodiments, the solidification agent includes solid PEG, for example PEG 1500 up to PEG 20,000. In certain embodiments, the PEG includes PEG 1450, PEG 3350, PEG 4500, PEG 8000, PEG 20,000, and the like. Additional suitable solidification agents include EO/PO block copolymers such as those sold under the tradenames Pluronic 108, Pluronic F68; amides such as lauric diethanolamide or cocodiethylene amide; and the like. In certain embodiments, the solidification agent includes a combination of solidification agents, such as combination of PEG and an EO/PO block copolymer (such as a Pluronic) and combination of PEG and an amide (such as lauric diethanolamide amide or stearic monoethanol amide).

Surfactants

In some embodiments, the compositions of the present invention include a surfactant. Surfactants suitable for use with the compositions of the present invention include, but are not limited to, nonionic surfactants, anionic surfactants, and zwitterionic surfactants.

Nonionic Surfactants

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC11; mixtures thereof, or the like.

Semi-Polar Nonionic Surfactants

The semi-polar type of nonionic surface active agents are another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

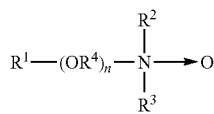

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof, $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of Formula 3:

$$R—O—(CH_2CH_2O)_n(CH_2)_m—CO_2X \qquad (3)$$

in which R is a $C_8$ to $C_{22}$ alkyl group or

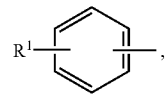

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In an embodiment, in Formula 3, n is an integer of 4 to 10 and m is 1. In an embodiment, in Formula 3, R is a $C_8$-$C_{16}$ alkyl group. In an embodiment, in Formula 3, R is a $C_{12}$-$C_{14}$ alkyl group, n is 4, and m is 1.

In an embodiment, in Formula 3, R is

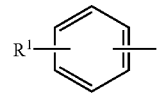

and $R^1$ is a $C_6$-$C_{12}$ alkyl group. In an embodiment, in Formula 3, $R^1$ is a $C_9$ alkyl group, n is 10 and m is 1. Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12}$-$C_{13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphate, or phosphono. Amphoteric surfactants are subdivided into two major classes known to those of skill in the art and described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

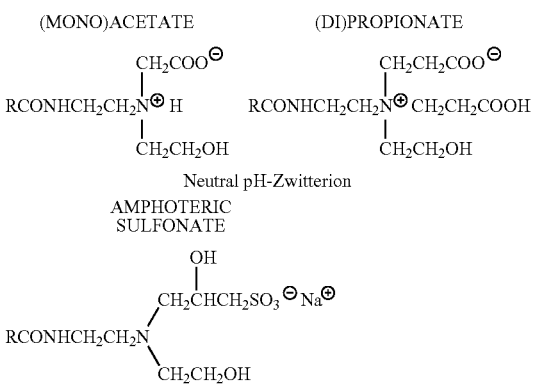

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R = C_8$-$C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—CH$_2$—CH$_2$—N$^+$(CH$_2$—CH$_2$—CO$_2$Na)$_2$—CH$_2$—CH$_2$—OH or $C_{12}$-alkyl-C(O)—N(H)—CH$_2$—CH$_2$—N$^+$(CH$_2$—CO$_2$Na)$_2$—CH$_2$—CH$_2$—OH.

Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

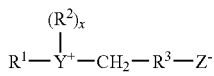

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

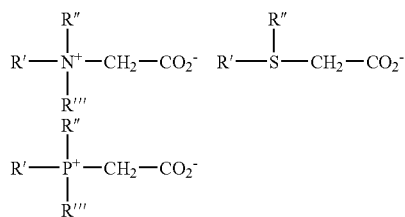

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO^{3-}$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Use Compositions

The compositions of the present invention include concentrate compositions and use compositions. For example, a concentrate composition can be diluted, for example with water, to form a use composition. In an embodiment, a concentrate composition can be diluted to a use solution before to application to an object. For reasons of economics, the concentrate can be marketed and an end user can dilute the concentrate with water or an aqueous diluent to a use solution.

The level of active components in the concentrate composition is dependent on the intended dilution factor and the desired activity of the sulfonated peroxycarboxylic acid compound. Generally, a dilution of about 1 fluid ounce to about 10 gallons of water to about 10 fluid ounces to about 1 gallon of water is used for aqueous compositions of the present invention. Higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 40 ounces of concentrate per 100 gallons of water. For example, a use composition can include about 0.01 to about 10 wt-% of a concentrate composition and about 90 to about 99.99 wt-% diluent; or about 0. 1 to about 1 wt-% of a concentrate composition and about 99 to about 99.9 wt-% diluent. Amounts of an ingredient in a use composition can be calculated from the amounts listed above for concentrate compositions and these dilution factors.

Methods Employing the Stabilized Peracid Compositions

In some aspects, the present invention includes methods of using the stabilized peracid compositions of the present invention. In some embodiments, these methods employ the antimicrobial and/or bleaching activity of the peracid. For example, the invention includes a method for reducing a microbial population, a method for reducing the population of a microorganism on skin, a method for treating a disease of skin, a method for reducing an odor, or a method for bleaching. These methods can operate on an object, surface, in a body or stream of water or a gas, or the like, by contacting the object, surface, body, or stream with a stabilized peracid composition of the invention. Contacting can include any of numerous methods for applying a composition, such as spraying the composition, immersing the object in the composition, foam or gel treating the object with the composition, or a combination thereof In some aspects, a composition of the present invention includes an amount of a stabilized peracid composition of the present invention effective for killing one or more of the food-borne pathogenic bacteria associated with a food product, including, but not limited to, *Salmonella typhimurium, Salmonella javiana, Campylobacter jejuni, Listeria monocytogenes,* and *Escherichia coli* O157:H7, yeast, and mold. In some embodiments, the compositions of the present invention include an amount of a stabilized peracid composition effective for killing one or more of the pathogenic bacteria associated with a health care surfaces and environments including, but not limited to, *Salmonella typhimurium, Staphylococcus aureus, Salmonella choleraesurus, Pseudomonas aeruginosa, Escherichia coli*, mycobacteria, yeast, and mold. The compositions and methods of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compositions and methods of the present invention, as described above, have activity against a wide variety of human pathogens. The present compositions and methods can kill a wide variety of microorganisms on a food processing surface, on the surface of a food product, in water used for washing or processing of food product, on a health care surface, or in a health care environment.

The compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic.

Suitable soft surfaces include, for example, paper; filter media, hospital and surgical linens and garments; soft-surface medical or surgical instruments and devices; and soft-surface packaging. Such soft surfaces can be made from a variety of materials including, for example, paper, fiber, woven or non-woven fabric, soft plastics and elastomers. The compositions of the invention can also be applied to soft surfaces such as food and skin (e.g., a hand). The present compositions can be employed as a foaming or nonfoaming environmental sanitizer or disinfectant.

The stabilized peracid compositions of the present invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs. The compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people. The compositions of the present invention can also be employed as an antimicrobial teat dip.

In some aspects, the compositions of the present invention can be employed for reducing the population of pathogenic microorganisms, such as pathogens of humans, animals, and the like. The compositions exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens can cause a variety of diseases and disorders, including mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The stabilized peracid compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like.

Particular foodstuffs that can be treated with compositions of the invention include, but are not limited to, eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

In some aspects, the compositions of the present invention are useful in the cleaning or sanitizing of containers, processing facilities, or equipment in the food service or food processing industries. The compositions have particular value for use on food packaging materials and equipment, and especially for cold or hot aseptic packaging. Examples of process facilities in which the composition of the invention can be employed include a milk line dairy, a continuous brewing system, food processing lines such as pumpable food systems and beverage lines, etc. Food service wares can be disinfected with the composition of the invention. For example, the compositions can also be used on or in ware wash machines, dishware, bottle washers, bottle chillers, warmers, third sink washers, cutting areas (e.g., water knives, slicers, cutters and saws) and egg washers.

Particular treatable surfaces include, but are not limited to, packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc. The compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like.

A filter containing stabilized peracid compositions of the present invention can reduce the population of microorganisms in air and liquids. Such a filter can remove water and air-born pathogens such as *Legionella*.

The present compositions can be employed for reducing the population of microbes, fruit flies, or other insect larva on a drain or other surface.

The compositions of the present invention can also be employed by dipping food processing equipment into the use solution, soaking the equipment for a time sufficient to sanitize the equipment, and wiping or draining excess solution off the equipment. The compositions of the present invention may be further employed by spraying or wiping food processing surfaces with the use solution, keeping the surfaces wet for a time sufficient to sanitize the surfaces, and removing excess solution by wiping, draining vertically, vacuuming, etc.

The compositions of the present invention may also be used in a method of sanitizing hard surfaces such as institutional type equipment, utensils, dishes, health care equipment or tools, and other hard surfaces.

The stabilized peracid compositions can be applied to microbes or to soiled or cleaned surfaces using a variety of methods. These methods can operate on an object, surface, in a body or stream of water or a gas, or the like, by contacting the object, surface, body, or stream with a composition of the invention. Contacting can include any of numerous methods for applying a composition, such as spraying the composition, immersing the object in the composition, foam or gel treating the object with the composition, or a combination thereof.

A concentrate or use concentration of a stabilized peracid composition of the present invention can be applied to or brought into contact with an object by any conventional method or apparatus for applying an antimicrobial or cleaning composition to an object. For example, the object can be wiped with, sprayed with, foamed on, and/or immersed in the composition, or a use solution made from the composition. The compositions can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered stabilized compositions according to the invention, or solutions containing these compositions.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Example 1

Storage Stability of Various Peracid Formulations

A composition including peracetic acid (POAA) and hydrogen peroxide ($H_2O_2$) was used as the base composition for this example. A series of formulations were prepared. These formulations included a source of magnesium ion both with and without 1-hydroxyethylidene diphosphonic acid (HEDP). A variety of magnesium ion sources were used including: magnesium oxide (MgO), magnesium sulfate anhydrous ($MgSO_4$), magnesium sulfate heptahydrate ($MgSO_4 \cdot 7H_2O$), and magnesium acetate tetrahydrate ($(CH_3COO)_2Mg \cdot 4H2O$). Each of the compositions prepared included about 21.0 wt % $H_2O_2$ (35%), and about 78 wt % acetic acid with varying amounts of $Mg^{2+}$, and HEDP. The source of $Mg^{2+}$ also varied.

The storage stability of the test solutions was measured. The amount of $H_2O_2$ and POAA remaining at 122° F. was measured at various time points. It was theorized that 24 days at 122° F. simulates 1 year at room temperature. The test results are shown in the tables below.

TABLE 1

Results when MgO used as Mg ion source and no chelating agent was present

| FORMULA # | Mg (PPM) | HEDP (wt %) | 70° F. Observations/ Appearance (24 hr) | $H_2O_2$/POAA 8 days 122° F. |
|---|---|---|---|---|
| CONTROL | None | 0.60 | Clear/colorless soln. | 1.69/10.15 |
| 1 | 1507 | None | Clear/colorless soln. | No peroxide or peracid found |
| 2 | 3014 | None | Clear/colorless soln. | No peroxide or peracid found |
| 3 | 4521 | None | Clear/colorless soln. | No peroxide or peracid found |
| 4 | 6028 | None | Clear/colorless soln. | No peroxide or peracid found |

TABLE 2

Results when $MgSO_4 \cdot 7H_2O$ used as Mg ion source (unless otherwise noted)

| FORMULA # | Mg (PPM) | HEDP (wt %) | 70° F. Observations Appearance (24 hr) | $H_2O_2$/POAA 6 days 122° F. | $H_2O_2$/POAA 24 days 122° F. |
|---|---|---|---|---|---|
| Theoretical Values | | | | 1.83/12.33 | 1.83/12.33 |
| CONTROL | 0 | 0.60 | Clear/colorless soln. | 1.69/10.15 | 0.78/4.42 |
| 5 | 1008 *used anhydrous | 0.60 | Solution not clear. | Titration not run. | Titration not run.. |
| 6 | 2016 *used anhydrous | 0.60 | | | |
| 7 | 49 | 0.60 | Initially clear; a granular precipitate in 24 hours. | 1.74/11.00 | 0.96/6.55 |
| 8 | 98 | 0.60 | | 1.75/10.88 | 0.96/5.86 |

TABLE 2-continued

Results when MgSO$_4$•7H$_2$O used as Mg ion source (unless otherwise noted)

| FORMULA # | Mg (PPM) | HEDP (wt %) | 70° F. Observations Appearance (24 hr) | H$_2$O$_2$/POAA 6 days 122° F. | H$_2$O$_2$/POAA 24 days 122° F. |
|---|---|---|---|---|---|
| 9 | 197 | 0.60 | Initially clear; flake-like precipitate in 24 hours. | 1.73/9.91 | 0.81/4.86 |
| 10 | 394 | 0.60 | | 1.76/10.00 | 0.78/5.21 |
| 11 | 49 | 0.90 | Clear, colorless solution. | 1.70/10.24 | 0.60/4.05 |
| 12 | 49 | 1.20 | Very small amount of precipitate noted on day 3. | 1.81/10.47 | 0.78/5.21 |
| 13 | 49 | 0 | Slightly hazy, colorless solution; no precipitate. | 0.07/0.79 | 0.0/0.01 |
| 14 | 98 | 0 | Slightly hazy, small amount precipitate (dusting). | 0.09/0.99 | 0.0/0.01 |
| 15 | 250 | 0.41 | Initially clear; flake-like precipitate on day 3. | 1.76/10.28 | 0.75/4.36 |
| 16 | 246 | 0 | Clear initially but sample quickly precipitated. | Titration not run. | Titration not run. |
| 17 | 492 | 0 | | | |
| 18 | 739 | 0 | | | |
| 19 | 985 | 0 | | | |

TABLE 3

Results when MgAcetate•4H$_2$O used as Mg ion source

| FORMULA # | Mg (PPM) | HEDP (wt %) | 70° F. Observations Appearance (24 hr) | H$_2$O$_2$/POAA 24 days 122 F. |
|---|---|---|---|---|
| Theoretical Calculation | | | | 1.83/12.33 |
| CONTROL | 0 | 0.60 | Clear, colorless solution. | 0.78/4.42 |
| 20 | 283 | 0 | Clear, colorless solution. | 0.00/0.00 |
| 21 | 566 | 0 | | |
| 22 | 849 | 0 | Bubbling | |
| 23 | 1132 | 0 | | |
| 24 | 2264 | 0 | | |
| 25 | 283 | 0.30 | Clear initially but sample Quickly precipitated. | Titrations not run. |
| 26 | 566 | 0.30 | | |
| 27 | 849 | 0.30 | | |
| 28 | 1132 | 0.30 | | |
| 29 | 226 | 0.60 | Initially clear/ course, granular precipitate next day. | 0.55/3.88 |
| 30 | 226 | 0.90 | Initially clear/ precipitate next day. | 0.69/4.41 |
| 31 | 226 | 1.20 | Initially clear, precipitate next day. | 0.76/4.73 |

From these studies, it was determined that Mg$^{2+}$ alone, i.e., without HEDP present, degrades the peracid present in solution (see Table 1). These results also showed that there was some stability enhancement at low levels of Mg$^{2+}$ (e.g., 49 and 98 ppm). These low levels were also at a low mole ratio of Mg$^{2+}$ to the HEDP (1:14 and 1:7 respectively). It was also determined that the stability enhancement progressively decreases at higher levels of Mg$^{2+}$, and adding more HEDP did not appear to increase the stability of the formulations.

Example 2

Solubility Studies of Mg$^{2+}$ and HEDP Complexes

Equal molar ratios of HEDP and MgSO$_4$.7H$_2$O were mixed with DI water, and the solubility's of the mixtures were observed. The results are shown in the table below.

TABLE 4

| HEDP (%) | MgSO$_4$•7H$_2$O (%) | % DI Water (balance) | Appearance 24 hours @ Ambient Temperature | Appearance 24 hours @ 122 F. |
|---|---|---|---|---|
| 1 | 0.717 | | Clear, colorless solution w/ no precipitation | Clear, colorless solution w/ no precipitation |
| 2 | 1.434 | | Clear, colorless solution w/ no precipitation | Clear, colorless solution w/ no precipitation |
| 3 | 2.151 | | Clear, colorless solution w/ no precipitation | Clear, colorless solution w/ no precipitation |
| 5 | 3.585 | | Clear, colorless solution w/ no precipitation | Clear, colorless solution w/ no precipitation |
| 10 | 7.17 | | Clear, colorless solution w/ no precipitation | Clear, colorless solution w/ no precipitation |

It was observed that in a neutral pH controlled by the HEDP, the mixtures were very soluble.

The effect of changes in pH on these mixtures were also measured. Mixtures containing equal molar levels of $Mg^{2+}$/HEDP complexes were tested in the systems shown below. The levels of $MgSO_4.7H_2O$ were chosen to be equal molar to the HEDP levels in the respective systems.

TABLE 5

| Test System | Acetic Acid (wt %) | HEDP (wt %) | $MgSO_4 \cdot 7H_2O$ (wt %) | DI Water (balance) | Appearance 24 hours | | |
|---|---|---|---|---|---|---|---|
| | | | | | 122° F. | Ambient | 40° F. |
| 1 | 11.2 | 1.6 | 1.1472 | | Clear, colorless solution w/ no precipitation. | Clear, colorless solution w/ no precipitation. | Clear, colorless solution w/ no precipitation. |
| 2 | 30 | 1.5 | 1.0755 | | | | |
| 3 | 59 | 1 | 0.717 | | | | |
| 4 | 78 | 1 | 0.717 | | Precipitation formed w/ addition of Acetic Acid. | | |

The results indicated that at higher levels of acetic acid, i.e., a more acidic pH, the complexes had a solubility problem For example, between 59% and 78% acetic acid, the pH is low enough that the $Mg^{2+}$/HEDP complexes develop solubility problems. Without wishing to be bound by any particular theory, it is thought that at such low pH conditions HEDP is only functioning minimally, as its conditional stability constants with problematic metal ions are reduced significantly.

Example 3

Stability Studies of Commercially Available Peracid Systems

The stability of a commercially available peracid solution, i.e., Tsunami 100, available from Ecolab Inc., after the addition of various $Mg^{2+}$/HEDP complexes was studied. Varying amounts of $MgSO_4.7H_2O$ were added to each sample, and all formulas contained 0.90% HEDP. The formulations were tested at room temperature and also at 122° F. The amount of $H_2O_2$ and POAA remaining in the formulations at varying time points was measured. The results are shown in the table below.

TABLE 6

| Formula | Wt % $MgSO_4 \cdot 7H_2O$ Added (ppm) | Room temperature | | 3 days at 122° F. | | 11 days at 122° F. | | 24 days at 122° F. | | 27 days at 122° F. | |
|---|---|---|---|---|---|---|---|---|---|---|---|
| | | % $H_2O_2$ | % POAA | % $H_2O_2$ | % POAA | % $H_2O_2$ | % POAA | % $H_2O_2$ | % POAA | % $H_2O_2$ | % POAA |
| Control | 0.0 | No data | No data | 11.74 | 12.96 | 10.98 | 12.37 | No data | No data | 10.11 | 11.85 |
| 1 | 0.02 wt % (19.7 ppm) | No data | No data | 12.33 | 11.77 | 11.34 | 12.56 | No data | No data | 10.67 | 12.47 |
| 2 | 0.05 wt % (49.3 ppm) | No data | No data | 12.21 | 12.36 | 11.09 | 12.62 | No data | No data | 10.28 | 13.05 |
| 3 | 0.20 wt % (197 ppm) | 11.46 | 14.62 | 11.92 | 13.99 | 11.40 | 14.62 | 11.57 | 13.32 | 11.30/ 10.86* | 13.50/ 14.34* |
| 4 | 0.40 wt % (394 ppm) | 11.43 | 14.78 | 11.85 | 14.10 | 11.57 | 14.16 | 11.60 | 13.52 | 10.96/ 10.85* | 13.89/ 14.56* |
| 5 | 0.60 wt % (591 ppm) | 11.31 | 15.04 | 11.79 | 13.99 | 11.48 | 14.58 | 11.46 | 13.65 | 11.34 | 13.75 |
| 6 | 0.80 wt % (788 ppm) | 11.24 | 14.65 | 11.87 | 14.05 | 11.47 | 14.26 | 11.31 | 13.96 | 11.22 | 13.73 |
| 7 | 1.00 wt % (985 ppm) | 11.39 | 14.94 | 12.25 | 13.12 | 11.56 | 14.21 | 11.37 | 14.00 | 11.10 | 13.74 |

*duplicate sample, unopened until day 28 (stored at 122° F.)

These results are also graphically depicted in FIG. 1. As can be seen from these results, the addition of MgSO$_4$.7H$_2$0 showed enhanced stabilities, i.e., more H$_2$O$_2$ and POAA remaining over time compared with a control. The most increased stability occurred around about 0.2 wt % and about 0.4 wt % Mg$^{2+}$ added.

The effect of MgSO$_4$.7H$_2$0 on Tsunami® use solutions was also tested. The test was run so as to simulate aseptic packaging conditions. The test formulations included 100 ppm of a mixture of hexanedioc acid dimethyl ester, and dimethyl sebecate and were tested at 140° F. The results are shown in the table below.

TABLE 7

| | % | % Conc. in | Ppm | Ppm Mg in | Use Soln. Initial | | Use Soln. 16 Hours at 140° F. | | Use Soln. 40 hours at 140° F. | |
|---|---|---|---|---|---|---|---|---|---|---|
| | POAA in conc. | Use Soln. | Mg in Conc. | Use Soln. | H$_2$O$_2$ (ppm) | POAA (ppm) | H$_2$O$_2$ (ppm) | POAA (ppm) | H$_2$O$_2$ (ppm) | POAA (ppm) |
| MgSO$_4$•7H$_2$O Added to concentrate | | | | | | | | | | |
| 0.20% (197 ppm) | 14.62 | 2.94 | 197 | 5.8 | 3300 | 4262 | 4068 | 2410 | 4644 | 1087 |
| 0.40 wt % (394 ppm) | 14.47 | 2.97 | 394 | 11.7 | 3362 | 4242 | 4100 | 2457 | 4712 | 1021 |
| 1.00 wt % (985 ppm) | 15.10 | 2.84 | 985 | 28 | 3200 | 4075 | 3900 | 2380 | 4500 | 1035 |
| none | 13.15 | 3.27 | None | None | 3463 | 4205 | 4310 | 2408 | 4900 | 1019 |
| MgSO$_4$•7H$_2$O Added to Use Soln. | | | | | | | | | | |
| 0.0128% | 13.15 | 3.27 | n/a | 12.5 | 3457 | 4287 | 4270 | 2432 | 4900 | 1151 |
| 0.0255% | 13.15 | 3.27 | n/a | 25 | 3500 | 4117 | 4275 | 2378 | 4925 | 1110 |
| 0.0638% | 13.15 | 3.27 | n/a | 63 | 3519 | 4115 | 4300 | 2370 | 4914 | 1047 |
| 0.1275% | 13.15 | 3.27 | n/a | 126 | 3442 | 4400 | 4241 | 2700 | 4858 | 1078 |

Figure 2:
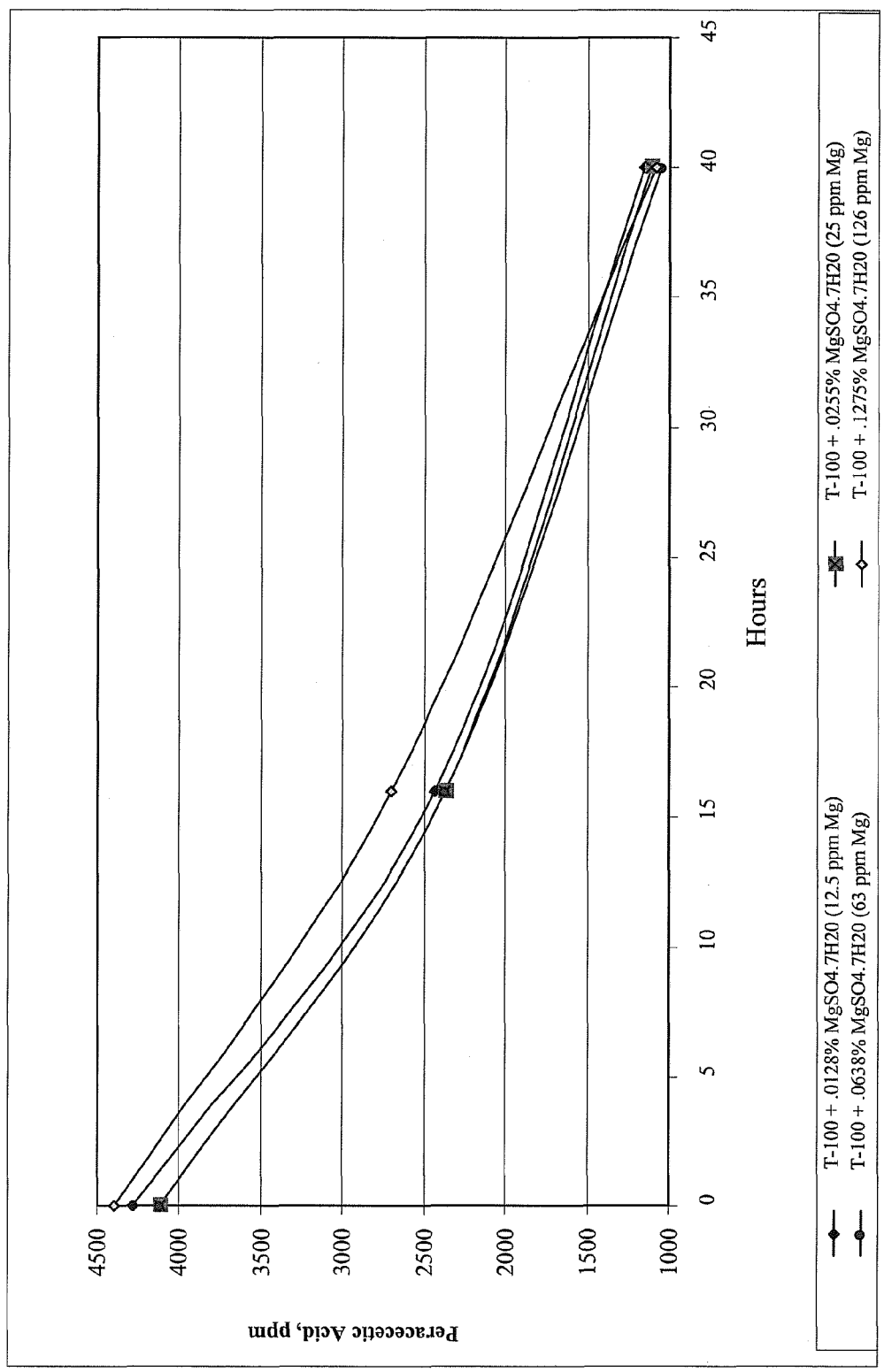
FIG. 2 graphically depicts the results of a storage stability study of a commercially available peracid formulation in combination with a stabilizing composition of the present invention.

These results are also graphically depicted in FIG. 2. As can be seen from these results, the results were relatively similar for all of the formulations tested.

Example 4

Figure 3:
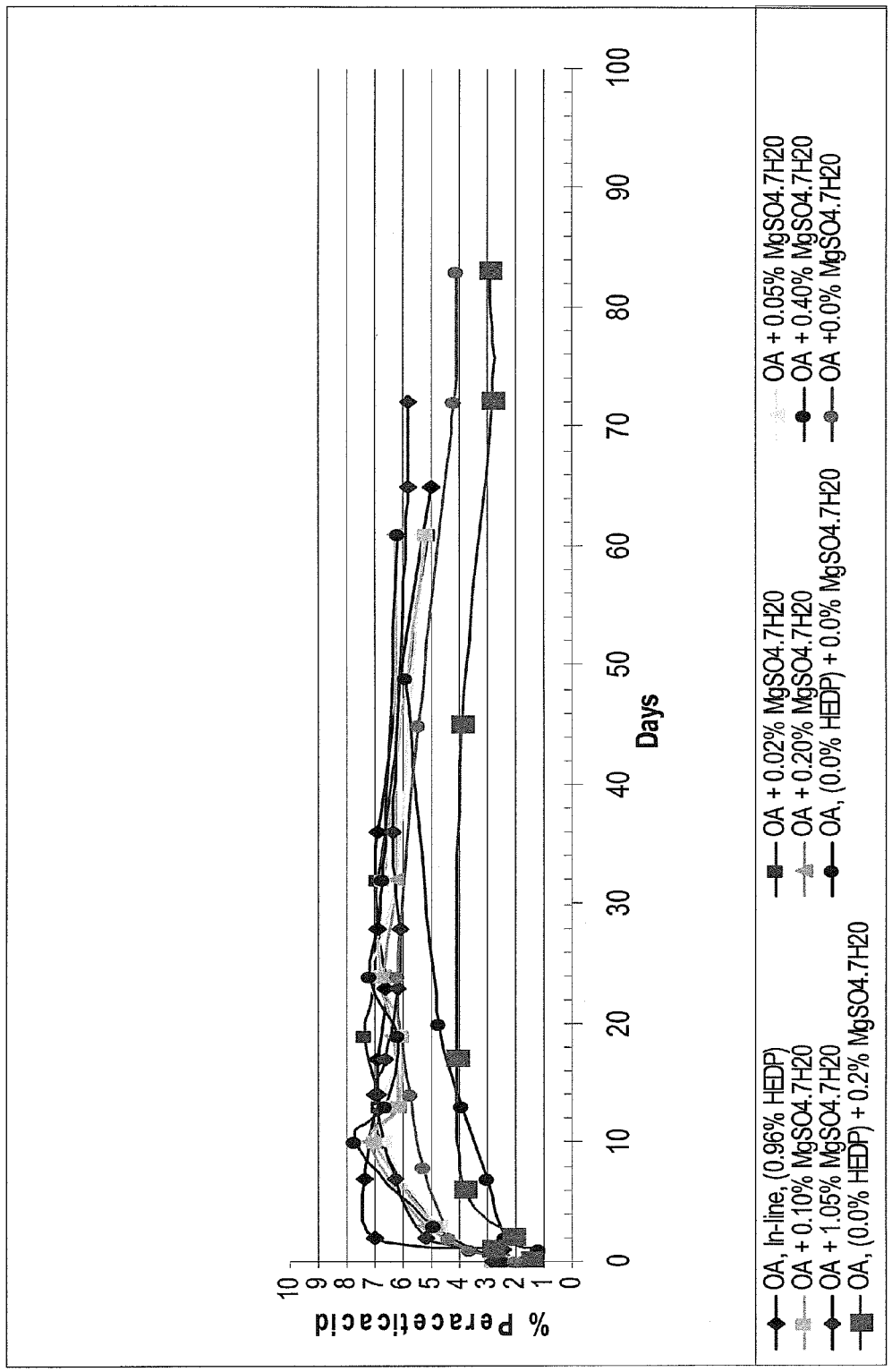
FIG. 3 graphically depicts the results of a storage stability study of a commercially available peracid formulation in combination with a stabilizing composition of the present invention.
Figure 4:
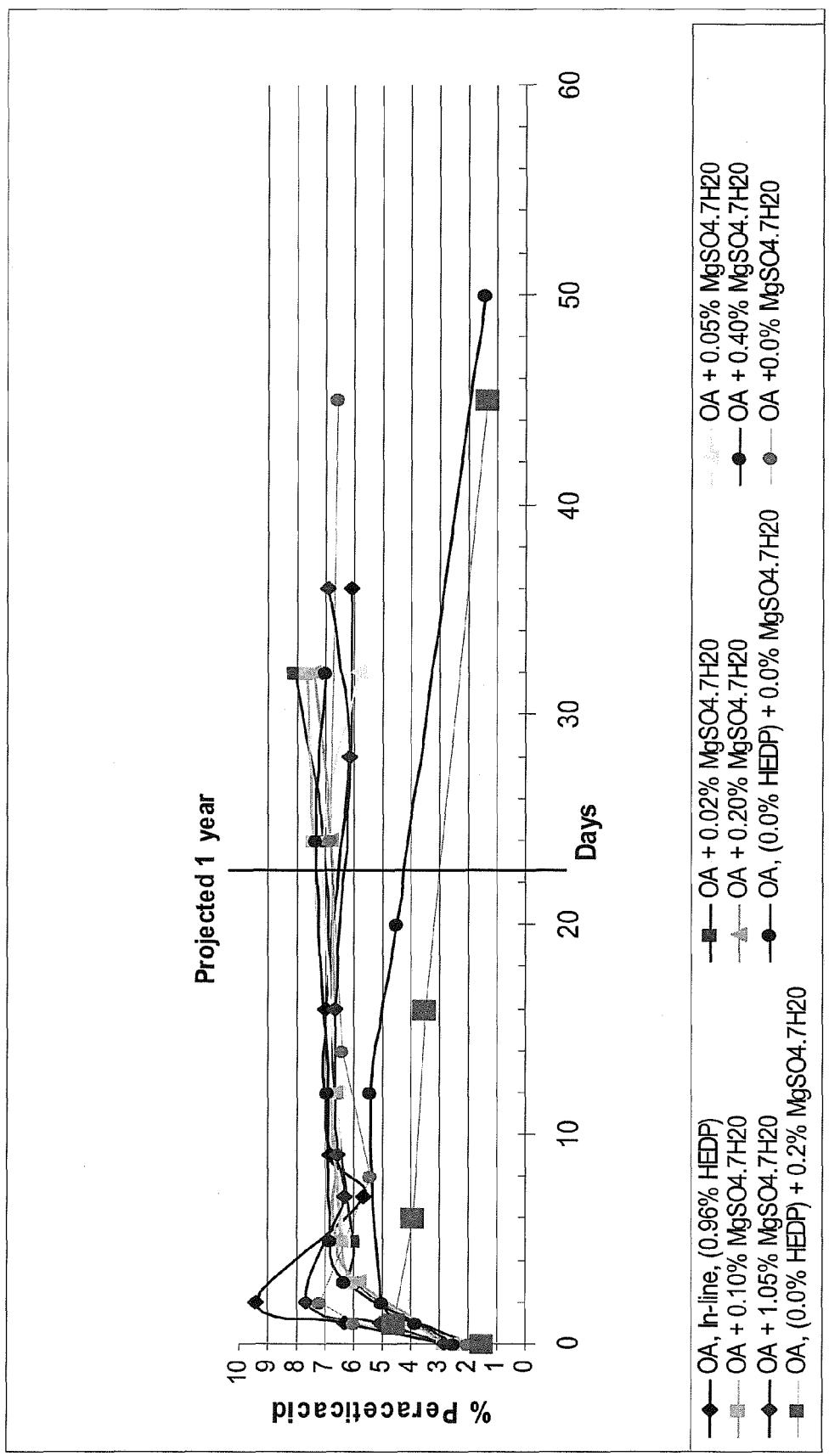
FIG. 4 graphically depicts the results of a storage stability study of a commercially available peracid formulation in combination with a stabilizing composition of the present invention.

Effect of the Addition of Mg$^{2-}$ on the Stability of Reduced Phosphorous Peracid Solutions A commercial peracid formulation, Oxonia Active, commercially available from Ecolab Inc., was used for this study. The formulation was altered such that it had about 0.1% phosphorous present in the formulation. Various amounts of MgSO$_4$.7H$_2$O were added to the formulations. The stabilities of these formulations were monitored and the results are shown in FIGS. 3 and 4.

As can be seen in these figures, without the addition of MgSO$_4$.7H$_2$O, the reduction of phosphorous (e.g., by reducing the level of HEDP acid) brings about two undesirable features in the formulas: the slower generation of peracetic acid; and reduced storage stability. These undesirable features were reduced with the addition of low levels of MgSO$_4$.7H$_2$O.

Example 5

Effect of Addition of Mg$^{2+}$ on a Mixed Peracid System

Figure 5:
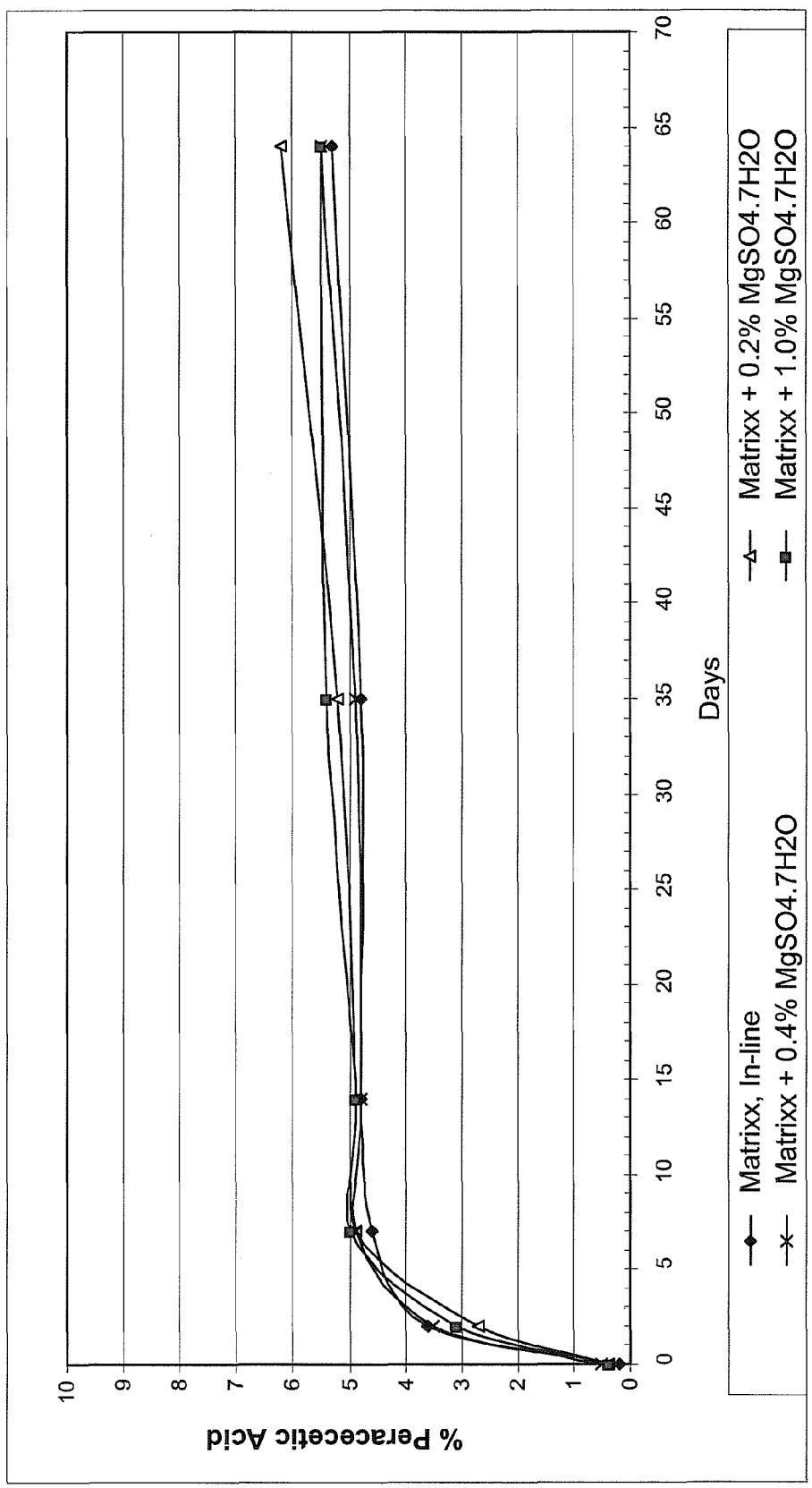
FIG. 5 graphically depicts the results of a storage stability study of a commercially available peracid formulation in combination with a stabilizing composition of the present invention at ambient temperature over 64 days.
Figure 6:
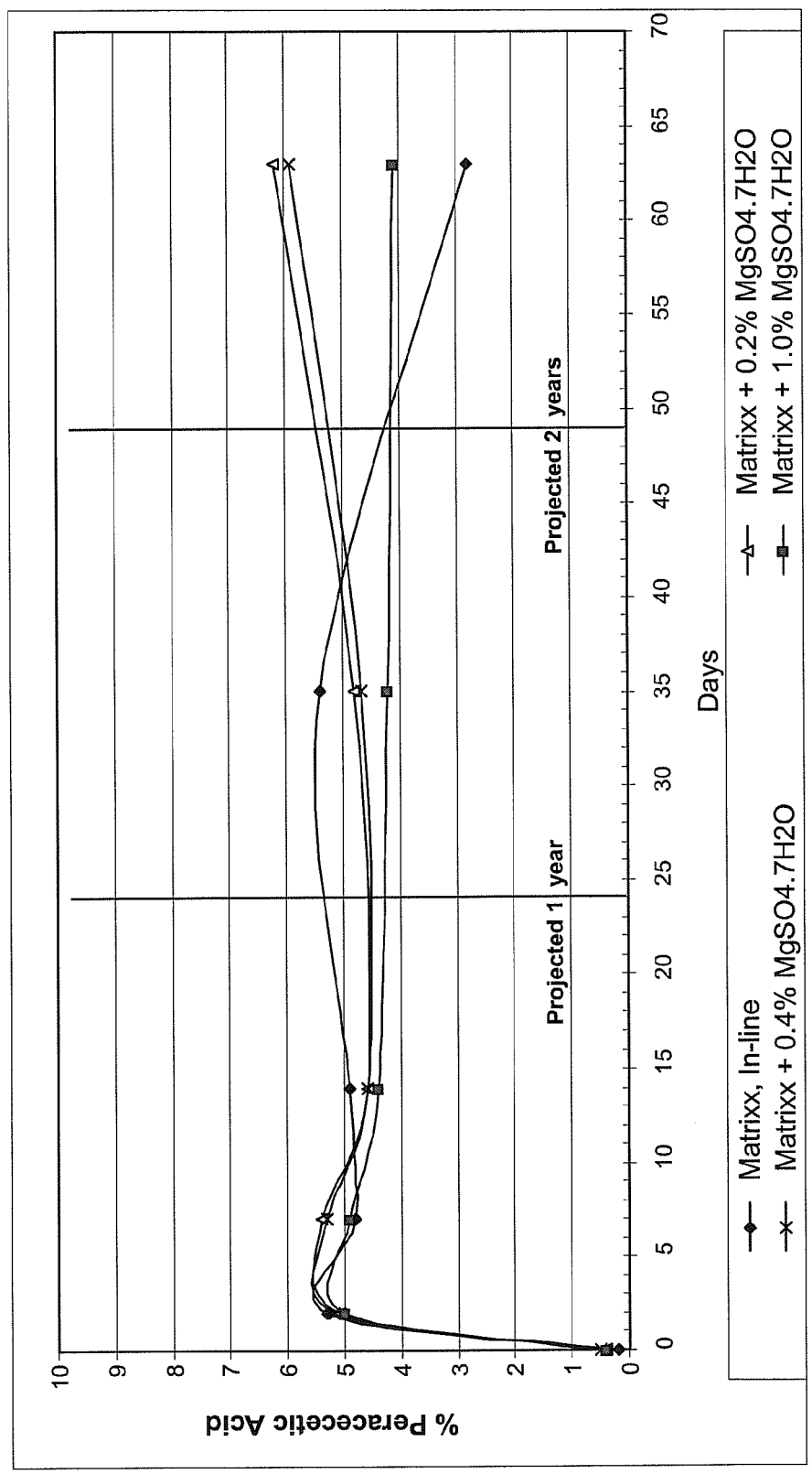
FIG. 6 graphically depicts the results of a storage stability study of a commercially available peracid formulation in combination with a stabilizing composition of the present invention at 120° F. over 63 days.

The effect of the addition of MgSO$_4$.7H$_2$O on a mixed peracid system including peroxyoctanoic acid (POAA) and peroxyacetic acid (POAA) was tested. Varying amounts of MgSO$_4$.7H$_2$O were added to compositions including POOA and POAA, as well as 0.9% HEDP. The amount of peracetic acid remaining over time was measured. The results are graphically depicted in FIG. 5.

As can be seen in this figure, the addition of MgSO$_4$.7H$_2$O showed a benefit after the simulated 1 year time frame.

OTHER EMBODIMENTS

It is to be understood that while the invention has been described in conjunction with the detailed description thereof, the foregoing description is intended to illustrate, and not limit the scope of the invention, which is defined by the scope of the appended claims. Other aspects, advantages, and modifications are within the scope of the following claims.

In addition, the contents of all patent publications discussed supra are incorporated in their entirety by this reference.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

We claim:

1. A stable aqueous peracid composition consisting of:
   (a) a peracid; and
   (b) a liquid stabilizing composition which is comprising a pre-reacted complex of a metal chelant selected from the group consisting of a calcium salt of EDTA, a magnesium salt of EDTA and mixtures thereof, wherein the stable peracid composition is substantially stable at room temperature for about 1 year.

2. The composition of claim 1, wherein the peracid is selected from the group consisting of peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxylactic, peroxymaleic, peroxyascorbic, peroxyhydroxyacetic, peroxyoxalic, peroxymalonic, peroxysuccinc, peroxyglutaric, peroxyadipic, peroxypimelic, peroxysubric acid and mixtures thereof.

3. The composition of claim 1, wherein the magnesium salt is selected from the group consisting of MgO, $MgSO_4$ anhydrous, $MgSO_4.7H_2O$, $MgAcetate.4H_2O$, MgAcetate anhydrous, and mixtures thereof.

4. The composition of claim 1, wherein the calcium salt is selected from the group consisting of calcium carbonate, calcium hydroxide, calcium arsenate, calcium carbide, calcium cyclamate, calcium gluconate, calcium permanganate, calcium phosphate, calcium phosphide, calcium stearate, calcium sulfate, calcium tungstate, hydroxylapatite and mixtures thereof.

5. The composition of claim 1, wherein the mole ratio of metal salt to chelating agent is about 5:1 to about 1:14.

6. The composition of claim 1, wherein the chelating agent is present in the stabilizing composition at about 0.5 wt% to about 5.0 wt%.

7. The composition of claim 1, wherein the stable peracid composition retains at least about 90% of the initial equilibrium peracid level for about 1 year at room temperature.

8. A method for forming a substantially stabilized peracid composition according to claim 1 comprising mixing:

components (a) and (b); such that a substantially peracid composition is formed, wherein the method does not include a drying step.

9. The method of claim 8, wherein the peracid is selected from the group consisting of peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxylactic, peroxymaleic, peroxyascorbic, peroxyhydroxyacetic, peroxyoxalic, peroxymalonic, peroxysuccinc, peroxyglutaric, peroxyadipic, peroxypimelic, peroxysubric acid and mixtures thereof.

10. The method of claim 8, wherein the magnesium salt is selected from the group consisting of MgO, $MgSO_4$ anhydrous, $MgSO_4.7H_2O$, $MgAcetate.4H_2O$, MgAcetate anhydrous and mixtures thereof.

11. The method of claim 8, wherein the mole ratio of the metal salt to the chelating agent is about 5:1 to about 1:14.

12. The method of claim 8, wherein the stabilized peracid composition is stable for about 1 year at room temperature.

13. The method of claim 8, wherein the peracid composition retains at least about 90% of the initial equilibrium peracid level for about 1 year at room temperature.

\* \* \* \* \*